(12) United States Patent
Boam et al.

(10) Patent No.: US 7,960,542 B2
(45) Date of Patent: Jun. 14, 2011

(54) PROCESS FOR PURIFYING OLIGONUCLEOTIDE SYNTHONS

(75) Inventors: Andrew Timothy Boam, London (GB); Andrew Guy Livingston, London (GB); Dinesh Nair, London (GB); Paul McCormac, Stirlingshire (GB); Stephen Hargreaves, Stirlingshire (GB)

(73) Assignee: Avecia Biotechnology, Inc., Milford, MA (US)

( * ) Notice: Subject to any disclaimer, the term of this patent is extended or adjusted under 35 U.S.C. 154(b) by 1443 days.

(21) Appl. No.: 10/539,202

(22) PCT Filed: Dec. 16, 2003

(86) PCT No.: PCT/GB03/05474
§ 371 (c)(1),
(2), (4) Date: Jan. 26, 2006

(87) PCT Pub. No.: WO2004/055037
PCT Pub. Date: Jul. 1, 2004

(65) Prior Publication Data
US 2006/0135760 A1    Jun. 22, 2006

(30) Foreign Application Priority Data
Dec. 18, 2002    (GB) .................................. 0229423.9

(51) Int. Cl.
*C07H 21/00*    (2006.01)
(52) U.S. Cl. ...................................................... 536/25.4
(58) Field of Classification Search .................. None
See application file for complete search history.

(56) References Cited

U.S. PATENT DOCUMENTS
4,415,732 A    11/1983    Caruthers et al.
5,026,838 A    6/1991    Nojiri et al.

FOREIGN PATENT DOCUMENTS
WO    98/15581    4/1998
WO    WO98/15581  *  4/1998
WO    03/087130    10/2003

OTHER PUBLICATIONS

Stawinski et al: "Nucleoside H-phosphonates. 12. Synthesis of nucleoside 3'-(hydrogen-phosphonothioate) monoesters via phosphinate intermediates" Journal of Organic Chemistry, American Chemical Society. Easton, US, No. 55, 1990, pp. 3503-3506, XP002075156 ISSN: 0022-3263 p. 3505.

Bhongle N N et al: "A Convenient Synthesis of Nucleoside 3'-H-Phosphonate Monoesters Using Triphosgene" Tetrahedron Letters, Elsevier Science Publishers, Amsterdam, NL, vol. 36, No. 38, Sep. 18, 1995, pp. 6803-6806, XP004027390 ISSN: 0040-4039 p. 6804, line 15-19.

Ozola V et al: "Use of Ammonium Aryl H-Phosphonates in the Preparation of Nucleoside H-Phosphonate Building Blocks" Tetrahedron Letters, Elsevier Science Publishers, Amsterdam, NL, vol. 37, No. 47, Nov. 18, 1996, pp. 8621-8624, XP004068732 ISSN: 0040-4039 p. 8623.

* cited by examiner

*Primary Examiner* — Traviss C McIntosh, III
(74) *Attorney, Agent, or Firm* — Timothy E. Tinkler

(57) ABSTRACT

A process for the purification of an oligonucleotide synthon is provided. The process comprises subjecting an organic solution comprising an oligonucleotide synthon and lower molecular weight impurities to nanofiltration whereby the ratio of an oligonucleotide synthon to lower molecular weight impurities in the solution is increased after the nanofiltration. Preferably, the oligonucleotide synthon is a nucleoside phosphoramidite or nucleoside H-phosphonate. The nanofiltration membrane is preferably a polyimide membrane having a molecular weight cut off of 400.

13 Claims, No Drawings

PROCESS FOR PURIFYING OLIGONUCLEOTIDE SYNTHONS

This is a 371 of PCT/GB03/05474, filed Dec. 16, 2003 and claiming the benefit of UK Application No. 0229423.9, filed Dec. 18, 2002.

The present invention concerns a process for the purification of synthons useful in the synthesis of oligonucleotides, and especially nucleoside phosphoramidites.

Synthetic oligonucleotides are important diagnostic tools for the detection of genetic and viral diseases. In addition, oligonucleotides and modified oligonucleotides are of interest as therapeutic candidates that inhibit gene expression or protein function. Large scale synthesis of oligonucleotides for use as therapeutic candidates has become increasingly important since FDA approval of an oligonucleotide analog for the treatment of cytomegalovirus (CMV), and several other oligonucleotide analogs are currently in clinical trials. Kilogram quantities of a purified oligonucleotide analog are needed for each clinical trial.

The principal method currently employed for the preparation of oligonucleotide is the phosphoramidite approach. The increasing demand for larger quantities of oligonucleotides has correspondingly increased demand for phosphoramidite compounds. Phosphoramidite compounds are commonly prepared by phosphitylation of a nucleoside with a phosphitylation agent in the presence of an activator. Hitherto, phosphoramidites have been purified by the use of lengthy and time consuming chromatography.

Alternative synthons for the synthesis of oligonucleotides include H-phosphonate compounds, and existing methods for the purification of these compounds suffer from similar disadvantages to phosphoramidites.

Alternative methods to purify synthons for oligonucleotides, especially methods applicable to large scale preparation are therefore necessary.

According to a first aspect of the present invention, there is provided a process for the purification of an oligonucleotide synthon, which comprises subjecting an organic solution comprising an oligonucleotide synthon and lower molecular weight impurities to nanofiltration whereby the ratio of an oligonucleotide synthon to lower molecular weight impurities in the solution is increased after the nanofiltration.

Oligonucleotide synthons which can be purified by the process according to the present invention include nucleoside or oligonucleotide phosphoramidites, nucleoside or oligonucleotide H-phosphonates, especially 3'- or 5'-terminal ribo or deoxyribonucleoside H-phosphonate monoesters, and nucleoside or oligonucleotide phosphoramidites.

The process according to the present invention is advantageously employed to purify protected nucleoside phosphoramidites. Preferred protected nucleoside phosphoramidites are deoxyribonucleoside-3'-phosphoramidite or ribonucleoside-3'-phosphoramidites. The invention is equally applicable to 5'-phosphoramidites.

Examples of preferred protected nucleoside phosphoramidites are compounds of formula (1):

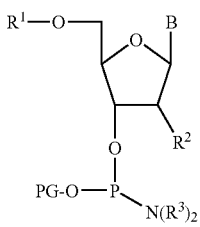

wherein $R^1$ is a protecting group, preferably a trityl, monomethoxytrityl or dimethoxytrityl group, B is a nucleoside base, $R^2$ represents —H, —F, —OR$^4$, —NR$^5$R$^6$, —SR$^7$, or a substituted or unsubstituted aliphatic group, such as methyl or allyl. PG is a phosphorus protecting group, commonly a cleavable phosphorus protecting group employed in oligonucleotide synthesis, and preferably a substituted or unsubstituted aliphatic group or a group of formula —OCH$_2$CH$_2$CN, —SCH$_2$CH$_2$CN, —OR$^8$, —SR$^8$, —O—CH$_2$CH$_2$—Si(CH$_3$)$_2$C$_6$H$_5$, —O—CH$_2$CH$_2$—S(O)$_2$—CH$_2$CH$_3$, —O—CH$_2$CH$_2$—C$_6$H$_4$—NO$_2$, —S—CH$_2$CH$_2$—Si(CH$_3$)$_2$C$_6$H$_5$, —S—CH$_2$CH$_2$—S(O)$_2$—CH$_2$CH$_3$, or —S—CH$_2$CH$_2$—C$_6$H$_4$—NO$_2$. $R^4$ represents —H, a substituted or unsubstituted aliphatic group (e.g., methyl, ethyl, methoxyethyl or allyl), a substituted or unsubstituted aryl group, a substituted or unsubstituted aralkyl, an alcohol protecting group, especially a base-labile or a silyl protecting group, or —(CH$_2$)$_q$—NR$^9$R$^{10}$. $R^5$ and $R^6$ are each, independently, —H, a substituted or unsubstituted aliphatic group, or an amine protecting group. Alternatively, $R^5$ and $R^6$ taken together with the nitrogen to which they are attached are a heterocyclyl group. $R^7$ represents —H, a substituted or unsubstituted aliphatic group, or a thiol protecting group. $R^9$ and $R^{10}$ are each, independently, —H, a substituted or unsubstituted aryl group, a substituted or unsubstituted heteroaryl group, a substituted or unsubstituted aliphatic group, a substituted or unsubstituted aralkyl group, a substituted or unsubstituted heteroaralkyl group or an amine protecting group. Alternatively, $R^9$ and $R^{10}$ taken together with the nitrogen to which they are attached form a heterocyclyl group. q is an integer from 1 to about 6. Each $R^3$ independently is a $C_{1-6}$ alkyl group, preferably an isopropyl group. The phosphoramidite employed is commonly a betacyanoethyloxy-N,N-diisopropyl phosphoramidite.

Nucleoside bases include naturally occurring bases, such as adenine, guanine, cytosine, thymine, and uracil and modified bases such as 7-deazaguanine, 7-deaza-8-azaguanine, 5-propynylcytosine, 5-propynyluracil, 7-deazaadenine, 7-deaza-8-azaadenine, 7-deaza-6-oxopurine, 6-oxopurine, 3-deazaadenosine, 2-oxo-5-methylpyrimidine, 2-oxo-4-methylthio-5-methylpyrimidine, 2-thiocarbonyl-4-oxo-5-methylpyrimidine, 4-oxo-5-methylpyrimidine, 2-amino-purine, 5-fluorouracil, 2,6-diaminopurine, 8-aminopurine, 4-triazolo-5-methylthymine, 4-triazolo-5-methyluracil and hypoxanthine.

The nucleoside base may be protected. Examples of suitable protecting groups are well known in the art. Typically, nucleoside bases have amine groups which can be protected with an amine protecting group, such as an amide or a carbamate. For example, the amine groups of adenine and cytosine are typically protected with benzoyl protecting groups, and the amine groups of guanine is typically protected with an isobutyryl group, a 4-isopropylphenoxyacetyl group or t-butylphenoxyacetyl group. However, other protection schemes, such as formamidine, may be used. For example, for fast deprotection, the primary amine groups of adenine and guanine are protected with phenoxyacetyl groups and the amine group of cytosine is protected with an isobutyryl group or an acetyl group.

It will be recognised that, whilst the formula (1) is expressed in terms of the natural, nucleosidic configuration (D-isomers), the present invention is equally applicable to the corresponding synthetic or unnatural configuration (L-isomers), to alpha and beta anomeric forms, and to mixtures of configurations.

H-phosphonates which may be purified by the process of the present invention are preferably nucleoside H-phosphonate monoesters, especially those having the general chemical formula (2):

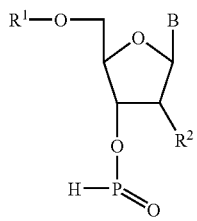

wherein $R^1$, $R^2$ and B are as described above for Formula (1).

Phosphoramidites which can be purified by the process according to the present invention are commonly the products of a reaction between a protected nucleoside comprising a free hydroxy group and a phosphitylation agent.

Phosphitylation agents commonly have the general chemical formula PG-O—$PX^1X^2$ wherein PG is as previously defined, and preferably a group of formula —$CH_2CH_2CN$; $X^1$ and $X^2$, which may be the same or different, represent leaving groups, such as halo, commonly bromo or chloro, or —$NR^{11}R^{12}$, wherein $R^{11}$ and $R^{12}$ each independently represents an alkyl, preferably a $C_{1-6}$ alkyl, group, or $R^{11}$ and $R^{12}$ are joined, together with the N to which they are attached, to form a 5-7 membered ring. Commonly, at least one of $X^1$ and $X^2$ is a group of formula —$NR^{11}R^{12}$. Most preferably, $X^1$ and $X^2$ are the same, and it is particularly preferred that both $X^1$ and $X^2$ are —$N[CH(CH_3)_2]_2$ groups.

Examples of preferred phosphitylating agents include O-β-cyanoethyl-N,N,N',N'-tetraisopropylphosphorodiamidite, (commonly known as "tetraphos"), O-β-cyanoethyl-N,N,N',N'-tetramethylphosphorodiamidite, O-β-cyanoethyl-N,N,N',N'-tetraethylphosphorodiamidite, bis(N,N-diisopropylamino)-2-methyltrifluoroacetylaminoethoxyphosphine, bis(N,N-diisopropylamino)-2-diphenylmethylsilylethoxyphosphine and O-β-cyanoethyl-bis(N-morpholino) phosphorodiamidite.

The lower molecular weight impurities predominantly comprise decomposition and side reaction products of the phosphitylation agent. Commonly, the impurities have a molecular weight of less than about 375, and preferably less than about 350.

In certain embodiments, the solvent present in the phosphoramidite solution produced in the phosphitylation process can be subject to a solvent change in order to produce a solution which is compatible with a wider range of nanofiltration membranes. For example, where the phosphitylation process employs a chlorocarbon solvent, especially dichloromethane, this can be exchanged for an alternative solvent, for example an ester, especially ethyl acetate. Further solvents which can be employed include ethers, such as tetrahydrofuran and dioxane, amides, such as dimethylformamide and N-methylpyrrolidinone, nitrile such as acetonitrile, and hydrocarbons such as hexane and toluene. A particularly preferred embodiment of the present invention comprises the nanofiltration of a solution of phosphoramidite in an ester solvent, especially ethyl acetate.

The phosphoramidite solution is advantageously treated, preferably prior to any solvent exchange, by contact with a basic solution, for example sodium carbonate solution, in order to neutralise acidic impurities.

The impurities present in H-phosphonate monoester oligonucleotide synthons which may be purified by the process of the present invention principally comprise by products derived from the reagents employed to introduce an H-phosphonate monoester moiety into a nucleoside, such reagents including ammonium salts of an aryl H-phosphonate monoesters, for example phenyl or alkylphenyl H-phosphonates.

Nanofiltration membranes that can be employed in the process of the present invention are selected to be resistant to degradation by the synthon solution. Examples of nanofiltration membranes include those made from poly(ethylene), poly(propylene), poly(sulphones), poly(ethersulphones), poly(tetrafluoroethylene), poly(vinylidenedifluoride), poly(amides), poly(imides), poly(acrylonitriles), cellulose acetate and mixtures thereof. The membranes may comprise components immobilised onto a support, for example a silicone immobilised onto a poly(acrylonitrile) support. Particular examples are those membranes disclosed in U.S. Pat. Nos. 4,368,112, 4,748,288, 4,985,138, 4,990,725, 5,067,970, 5,093,002, 5,102,551, 5,205,934 and 5,265,734 and WO00/06293 (incorporated herein by reference). For the purification of many oligonucleotide synthons, especially nucleoside phosphoramidites and H-phosphonates, the membranes are commonly selected to have a molecular weight cut off at about 400. That is, the membrane allows the passage of compounds having a molecular weight of less than 400, but does not allow the passage of compounds having a greater molecular weight. Particularly suitable membranes are those disclosed in U.S. Pat. No. 5,264,166 (incorporated herein by reference).

In the process according to the present invention, "crude" solutions containing oligonucleotide synthon are passed through the nanofiltration membrane, commonly using high pressure. The synthon is not permitted to pass through the nanofiltration membrane, whereas the lower molecular weight impurities are able to pass through. The nanofiltration residues comprising the synthon (retentate) can be washed with further fresh solvent. Commonly, the passage across the membrane continues until the volume of synthon solution residue is significantly lower than the original "crude" solution, thereby simultaneously effecting purifying and concentrating the synthon. The process may be carried out using apparatus known in the art for nanofiltration, and in particular using apparatus as disclosed in WO02/076588 (incorporated herein by reference). Either dead-end filtration or cross-flow filtration configurations may be employed. Passage across the membrane may be achieved by the use of a pump, or by alternative means, for example by gas pressure, such as nitrogen.

In certain embodiments, a volume of fresh organic solvent corresponding to the volume passed through the nanofiltration membrane is added into the retained synthon solution, and the process continued until the desired purity is achieved. The fresh solvent can be added continuously at a rate corresponding to the rate of passage through the nanofiltration membrane (constant volume), or can be added in one or more batches at intervals (variable volume) during the purification. The addition of fresh solvent can prevent the synthon solution from becoming excessively viscous, and help to maintain flux rates across the membrane. Once the desired purity is achieved, solvent can continue to be passed across the nanofiltration membrane to increase the concentration of the synthon.

The process according to the present invention is often carried out at a temperature in the range of from 0° C. to about 50° C., and preferably at ambient temperature, such as from about 15° C. to about 30° C.

When high-pressure is employed, it will be recognised that the actual upper limit of the pressure that can be employed will be determined by the ability of the membrane to maintain its integrity under such pressures. In many embodiments, pressures of up to 60 bar, especially up to 50 bar, and particularly pressures in the range of from 15 to 35 bar, such as about 30 bar, can be employed.

The "crude" solutions which can be purified by the process according to the present invention commonly comprise up to about 40% by weight of synthon, preferably from about 2-10% w/w.

The purified synthon may then be recovered from the residue by conventional methods.

The present invention is illustrated without limitation by the following examples.

Example 1

A high pressure filtration cell configured for dead-end operation was fitted with a 14 cm² disk polyimide 400 molecular weight cut-off nanofiltration membrane (STARMEM™ 240) commercially available from Grace Davison Membranes, and a Stuart stirrer, high pressure being provided by connection to a nitrogen cylinder via a high-pressure regulator. The membrane was pre-conditioned by passing ethyl acetate through the membrane under a pressure of 30 bar until constant flux was achieved. 35 cm³ of an ethyl acetate solution of reaction product from the preparation of N-benzoyl protected 5'-O-dimethoxytrityl-2'-deoxycytidine-3'-(2-cyanoethyl-N,N-diisopropyl) phosphoramidite (dC amidite) by reaction with tetraphos, containing 30% w/w of dC amidite, was charged to the filtration cell, and passed through the membrane under 30 bar pressure until 16.5 cm³ of permeate was obtained. The retentate was removed from the filtration vessel and analysed for amidite and hydrolysed tetraphos (an impurity by-product from the amidite preparation) content.

The weight ratio of dC amidite to hydrolysed tetraphos in the crude solution was 23.5:1, the corresponding ratio in the purified retentate was 31.1:1.

Example 2

The process of Example 1 was repeated, except that a crude solution of 30% w/w N-benzoyl protected 5'-O-dimethoxytrityl-2'-deoxyadenosine-3'-(2-cyanoethyl-N,N-diisopropyl) phosphoramidite (dA amidite) reaction product was employed, and 16 cm³ of permeate was obtained.

The weight ratio of dA amidite to hydrolysed tetraphos in the crude solution was 62.4:1, the corresponding ratio in the purified retentate was 75.1:1.

Example 3

A high pressure filter cell configured for cross-flow operation was fitted with a 78.5 cm² disk polyimide 400 molecular weight cut-off nanofiltration membrane (STARMEM™ 240) commercially available from Grace Davison Membranes. The membrane was preconditioned by passage of ethyl acetate under a pressure of 30 bar until constant flux was achieved. 2 l of an ethyl acetate solution of reaction product from the preparation of N-2-isobutyryl protected 5'-O-dimethoxytrityl-2'-deoxyguanosine-3'-(2-cyanoethyl-N,N-diisopropyl) phosphoramidite (dG amidite) by reaction with tetraphos, containing 5% w/w of dG amidite, was circulated from a holding tank, through the filtration cell at a pressure of 30 bar, and this retentate returned to the holding tank. Permeate through the nanofiltration membrane was collected separately. The circulation was continued until 1.5 l of permeate was obtained. The retentate was analysed for amidite and hydrolysed tetraphos content.

The weight ratio of dG amidite to hydrolysed tetraphos in the crude solution was 15.5:1, the corresponding ratio in the purified retentate was 21.6:1.

The invention claimed is:

1. A process for the purification of a nucleoside phosphoramidite or nucleoside H-phosphonate oligonucleotide synthon from an organic solution of a nucleoside phosphoramidite or nucleoside H-phosphonate oligonucleotide synthon and lower molecular weight impurities, which comprises subjecting said organic solution to nanofiltration whereby the ratio of synthon to lower molecular weight impurities in the solution is increased after the nanofiltration.

2. A process according to claim 1, wherein the oligonucleotide synthon is a compound of formula (1):

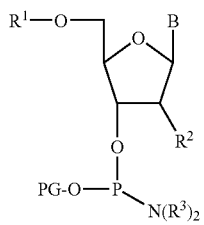

wherein $R^1$ is a protecting group, B is a nucleoside base, $R^2$ represents —H, —F, —OR⁴, —NR⁵R⁶, —SR⁷, or aliphatic group, each $R^3$ independently is a $C_{1-6}$ alkyl group, PG is a phosphorus protecting group, $R^4$ represents —H, an aliphatic group, an aryl group, an aralkyl, an alcohol protecting group, or —(CH₂)$_q$—NR⁹R¹⁰, $R^5$ and $R^6$ are each, independently, —H, an aliphatic group, or an amine protecting group, or $R^5$ and $R^6$ taken together with the nitrogen to which they are attached are a heterocyclyl group, $R^7$ represents —H, an aliphatic group, or a thiol protecting group, $R^9$ and $R^{10}$ are each, independently, —H, an aryl group, a heteroaryl group, an aliphatic group, an aralkyl group, a heteroaralkyl group or an amine protecting group, or $R^9$ and $R^{10}$ taken together with the nitrogen to which they are attached form a heterocyclyl group; and q is an integer from 1 to about 6.

3. A process according to claim 2, wherein PG is a beta-cyanoethyl group, and each $R^3$ is an isopropyl group.

4. A process according to claim 1, wherein a polyimide nanofiltration membrane is employed.

5. A process according to claim 1, wherein a nanofiltration membrane having a molecular weight cut off of 400 is employed.

6. A process according to claim 1, wherein the process is operated in cross flow configuration.

7. A process according to claim 1, wherein the process employs a pressure of from 15 to 35 bar.

8. A process according to claim 1, wherein fresh organic solvent corresponding to the volume passed through the nanofiltration membrane is added into the retained synthon solution.

9. A process according to any one of claims 1 to 3, wherein a polyimide nanofiltration membrane having a molecular weight cut-off of 400 is employed.

10. A process according to claim 9, wherein the process is operated in cross flow configuration.

11. A process according to any one of claims 1 to 3, wherein a polyimide nanofiltration membrane is employed and fresh organic solvent corresponding to the volume passed through the nanofiltration membrane is added into the retained synthon solution.

12. A process according to claim 11, wherein a polyimide nanofiltration membrane having a molecular weight cut-off of 400 is employed.

13. A process according to claim 12, wherein the process is operated in cross flow configuration.

* * * * *